United States Patent [19]

Bezanson

[11] Patent Number: 5,106,187
[45] Date of Patent: Apr. 21, 1992

[54] METHOD AND APPARATUS FOR THE INDENTIFICATION OF PARTICLES

[75] Inventor: Donald S. Bezanson, Nova Scotia, Canada

[73] Assignee: Maritime Scientific Services Ltd., Nova Scotia, Canada

[21] Appl. No.: 426,680

[22] Filed: Oct. 26, 1989

[30] Foreign Application Priority Data

Mar. 31, 1989 [CA] Canada .................................. 595362

[51] Int. Cl.$^5$ ............................................. G01N 21/84
[52] U.S. Cl. ...................................... 356/73; 356/39; 356/337
[58] Field of Search ................. 356/73, 337, 338, 341, 356/343, 335, 336, 344, 39; 73/861.02, 861.04, 861.12, 861.14

[56] References Cited

U.S. PATENT DOCUMENTS

| | | | |
|---|---|---|---|
| 3,871,770 | 3/1975 | von Behrens et al. | 356/39 |
| 4,475,236 | 10/1984 | Hoffman | 382/6 |
| 4,510,438 | 4/1985 | Aver | 386/72 |
| 4,596,464 | 6/1986 | Hoffman | 382/6 |
| 4,765,737 | 9/1988 | Harris et al. | 356/73 |
| 4,790,653 | 12/1988 | North, Jr. | 356/73 |

Primary Examiner—Vincent P. McGraw
Assistant Examiner—LaCharles P. Keesee
Attorney, Agent, or Firm—Jones, Tullar & Cooper

[57] ABSTRACT

Apparatus for analyzing particles in which the particles traverse a sensing zone one at a time. A first detector measures variations in the conductivity of the fluid caused by the presence of a particle in the sensing zone. A laser irradiates the sensing zone and a second detector is provided responsive to light scattered by particles in the sensing zone. Additional detectors are provided responsive to fluorescence from the particles. The signals from each of the detector means are digitized and stored and then compared. The differences in successive waveforms from each detector indicate the presence of abnormal particles. Waveform shape is also used as an indication of the shape of the particles.

13 Claims, 4 Drawing Sheets

METHOD AND APPARATUS FOR THE INDENTIFICATION OF PARTICLES

BACKGROUND OF THE INVENTION

1. Field of the Invention

This application relates to apparatus for the detection and analysis of small particles in fluids and, in particular, to apparatus of this type including circuitry for the storage and processing of signals representing the detected particles.

The apparatus of this invention is particularly useful in the monitoring of industrial processes and the identification of various particles without the intervention of human operators. Typical applications are in oceanography or industrial applications such as milk analysis.

2. Prior Art

It is known to use a Coulter detector to establish particle size by having the particles carried in a conductive liquid. When a particle encounters a restriction in its flow path it displaces a significant amount of the conductive liquid with a resulting change in conductivity giving an indication of particle size. It is also known to detect and analyse small particles and fluids by causing the particles to traverse singly across the sensing zone irradiated by coherent light from a laser. As shown in U.S. Pat. No. 4,596,464 issued to Hoffman on June 24, 1986 scattered light is detected and analysed to give information as to the characteristics of a particle. The particles may also fluoresce in the sensing zone and the resulting fluorescence is similarly detected and analysed to give information about a particle. This is shown in U.S. Pat. No. 4,475,236 issued to Hoffman on Oct. 2, 1984. If the particles are not themselves fluorescent then an appropriate dye may be added to the sample to produce fluorescence.

SUMMARY OF THE INVENTION

The present application relates to an improved apparatus which enables the signal from each of the conductivity, scattering and fluorescent detectors to be stored as separate waveforms so that the various waveforms relating to a single particle can be used as a composite source of information to establish the identity and characteristics of a particle.

Briefly expressed the present application relates to apparatus for the detection and analysis of particles in fluids comprising, a restriction defining a restricted flow path for the fluid whereby the particles traverse a sensing zone in the flow path immediately downstream from the restriction one at a time. A first detector measures variations in the conductivity caused by the presence of a particle in the restriction. A laser irradiates the region immediately downstream from the conductivity restriction. A second detector is responsive to light scattered by a particle in the laser beam, and further detectors are responsive to fluorescence from the particle. The signals from each of the detector means are digitized and stored and then compared.

BRIEF DESCRIPTION OF THE DRAWINGS

A particular embodiment of the invention will now be described in conjunction with the accompanied drawings in which.

DETAILED DESCRIPTION OF THE INVENTION

Figure 1:
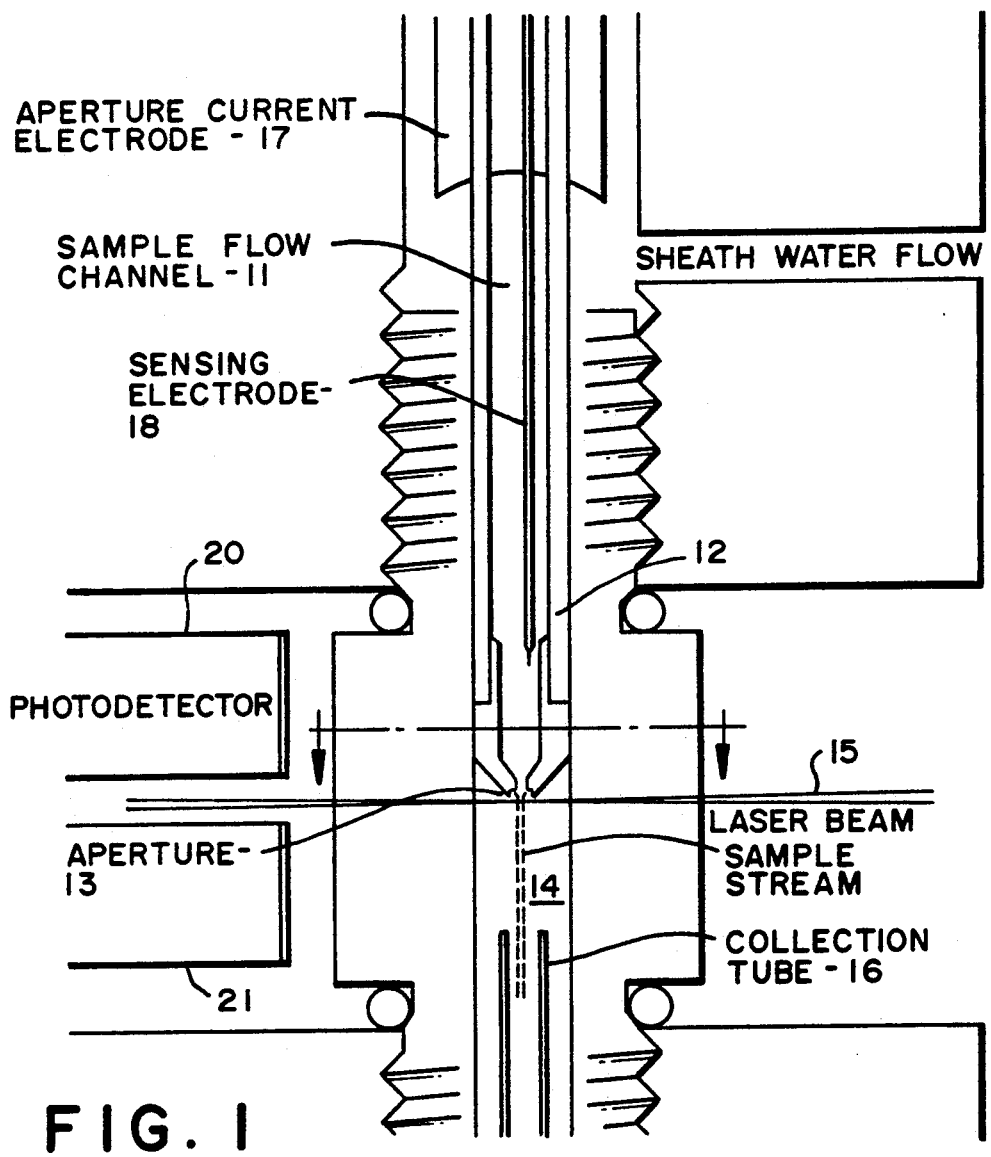
FIG. 1 is a diagram of the flow cell which includes the sensing zone with FIG. 1(a) showing a cross-section of the sensing zone.
Figure 1A:
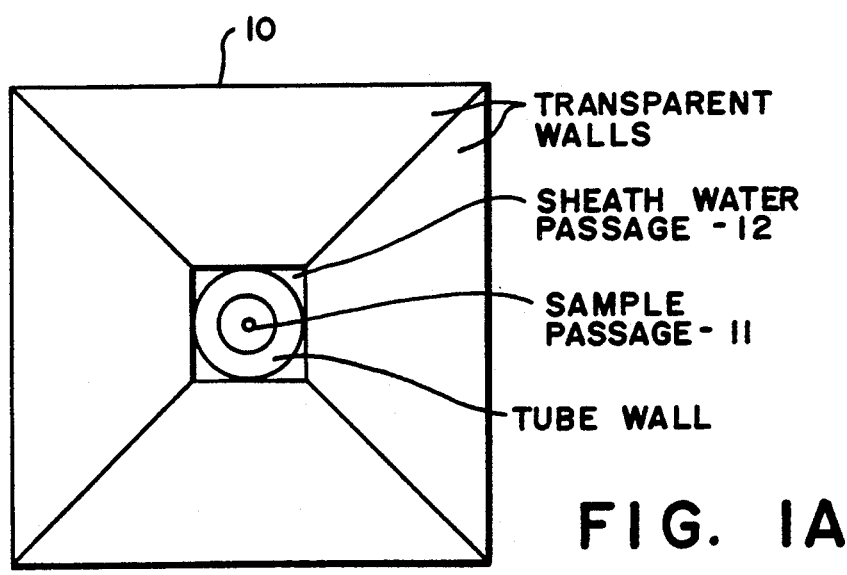

FIG. 1 shows a flow cell formed from a body 10 defining a sample fluid channel 11 and a sheath fluid channel 12. The sample fluid passes through an aperture 13 which controls the size of the sample stream and the resulting thin stream, about 50–200 $\mu$m diameter, passes through a sensing zone 14 contained in a cuvette portion of the flow cell. A transverse beam of radiant energy 15 from a laser 18 (FIG. 2) passes through the sensing zone to illuminate particles therein. A collection tube 16 separates the sample flow from the sheath fluid flow at the outlet so that the samples are available for retesting.

Thus, the sample fluid is passed in a thin stream through the sensing zone with the stream surrounded by a sheath flow of clean fluid. As a result only one particle traverses the sensing zone at any one time. Electrodes 17 are provided in contact with this sheath fluid and the sample fluid. Sheath and sample water have a certain conductivity and the electric current caused to flow through the orifice between the electrodes 17 creates a voltage drop across it. As a particle in the flow displaces conductive fluid, the effective resistance of the orifice rises and the voltage rises. This voltage change is sensed by electrode 18. The ratio of the change in voltage to the background voltage is recorded as proportional to the volume of the particle.

In the sensing zone the laser beam is focused about 10 $\mu$m along the streamline and about 100 $\mu$m wide across it. In the laser beam the particle scatters light and any fluorescent material in it fluoresces at a characteristic colour and intensity. The scattered light is detected by two or more photodetectors 20, 21 adjacent to the exiting beam and almost colinear (in the range 1°–20°) with the input beam. Fluorescent light emitted in conical detection zones at right angles to the input beam is gathered by condensing lenses (not shown) and transmitted to photomultiplier tubes (not shown) to amplify the low amounts of energy in this signal. These detectors are responsive to different wavelengths, typically one in the red ends of the spectrum and one in the green.

The collection tube 16 serves to collect the sample particles which have passed through the sensing zone so that they are then available for retesting. In the sensing zone the particles are travelling at a higher velocity than the sheath fluid and accumulate in tube 16. By controlling the rate of withdrawal at the outlet of tube 16 a sample fluid flow close to that of the original is obtained.

Figure 2:
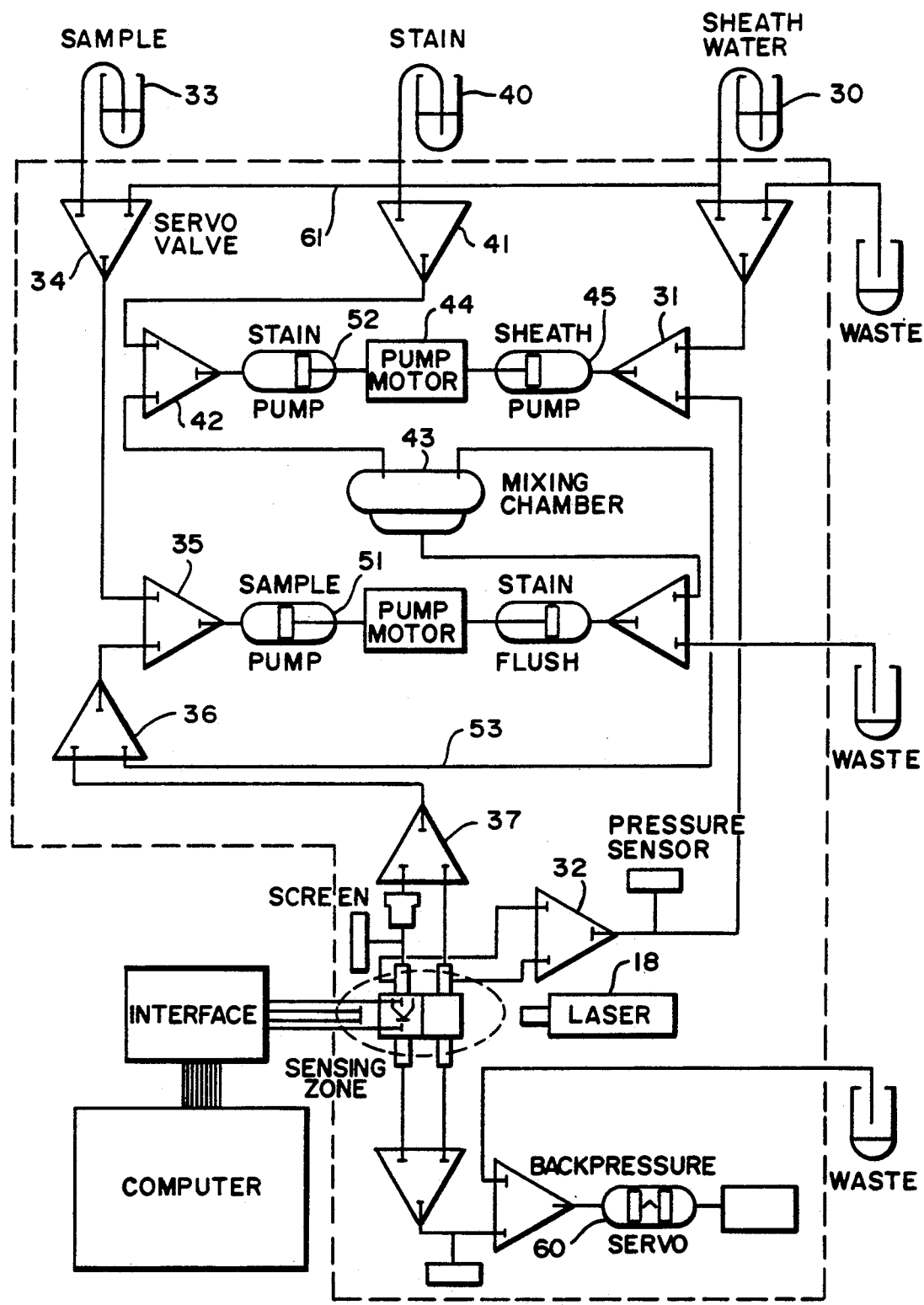
FIG. 2 is a diagram of the fluid supply system.

A block diagram of the system including sensors, interface, computer, and fluid control system is shown in FIG. 2. The triangular elements, such as valve 34, are computer-controlled solenoid valves. Fluid is driven by computer-controlled stepper motors, such as motor 44, connected to syringe pumps, such as pump 45. Beaker shapes indicate sources of fluids outside the machine, such as sample source 33. Connections from the computer to the solenoids and motors, and from pressure sensors, are not shown.

Sheath fluid is drawn from a source 30 through solenoid control valves 31 and 32 to be injected into the flow cell. The flow is controlled by pump 45 which has a variable rate, typically operating at 1 ml./minute. Two flow cells are shown, one equipped with a screen 50 to exclude potentially clogging particles and having a small diameter orifice for measuring small sized particles. The other is for measuring larger particles. Valve 32 selects between the flow cells for the sheath fluid and valve 37 selects between the cells for the sample fluid. The sample fluid is drawn from a source 33 through control valves 34, 35, 36 and 37 and is also injected into the selected flow cell. The sample fluid flow is controlled by pump 51. If required, the sample can be mixed with stain from a source 40 supplied to a mixing chamber 43 via valves 41 and 42 under control of pump 52. The mixing is achieved by supplying sample fluid to the mixing chamber via line 53 through valve 36. Once mixed, the fluid is returned along the same line to be fed to the flow cell.

Thus, in operation, sample fluid and sheath fluid are first drawn into their respective syringe pumps and the valves repositioned for injection into one of the two flow cells, one for small, one for large particles. Sample and sheath are then pumped through at optimum rates. Sample pumping rate determines the rate of particle detection which is usefully the maximum below interface overload. The sheath pumping rate controls particle speed in the sensing zone and may be varied with particle size range for optimum waveform resolution. Rather than using collection tube 16 the fluid mix can pass to a receiving syringe pump 60 which moves in tandem with the input pumps, while generating a constant backpressure through a compressed spring. This reduces bubbling across the orifice plate and passes higher currents to be used in electrodes 17, leading to operator sensitivity. The connection 61 between source 30 and valve 34 permits the flushing of stain solution.

Figure 3:
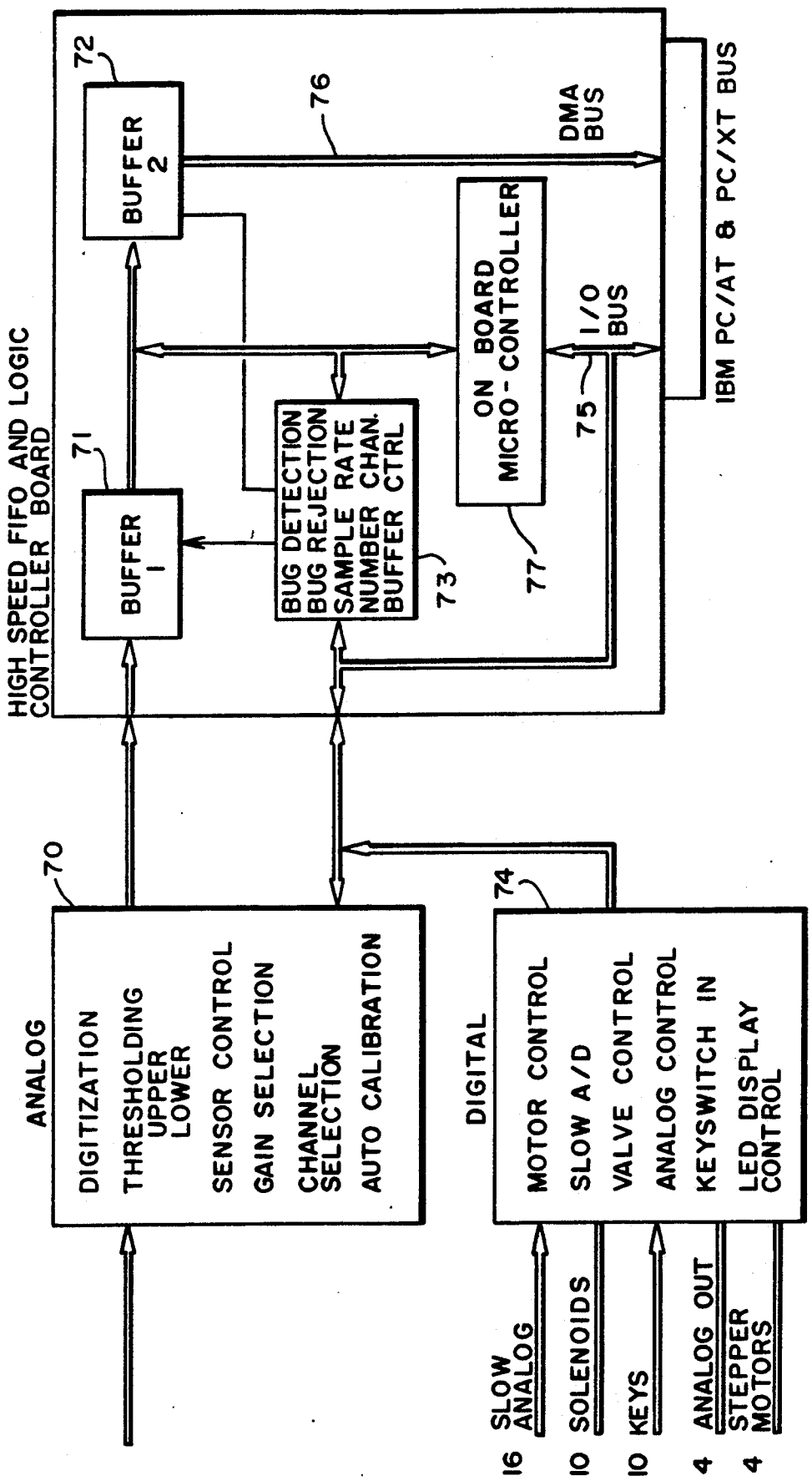
FIG. 3 is a block diagram of the data processing and storage section.

Referring now to the block diagram of FIG. 3, four analog boards 70 are provided, typically connected to the conductivity signal, the scatter signal and the two fluorescence signals. These signals are digitised and transferred to buffers 71 and 72. At the same time a determination if the signals are within preset limits is made in board 73 and appropriate control signals supplied to board 74 to control the valves and pumps. Bus 75 and bus 76 are connected to the computer for long term storage and signal processing.

Figure 4:
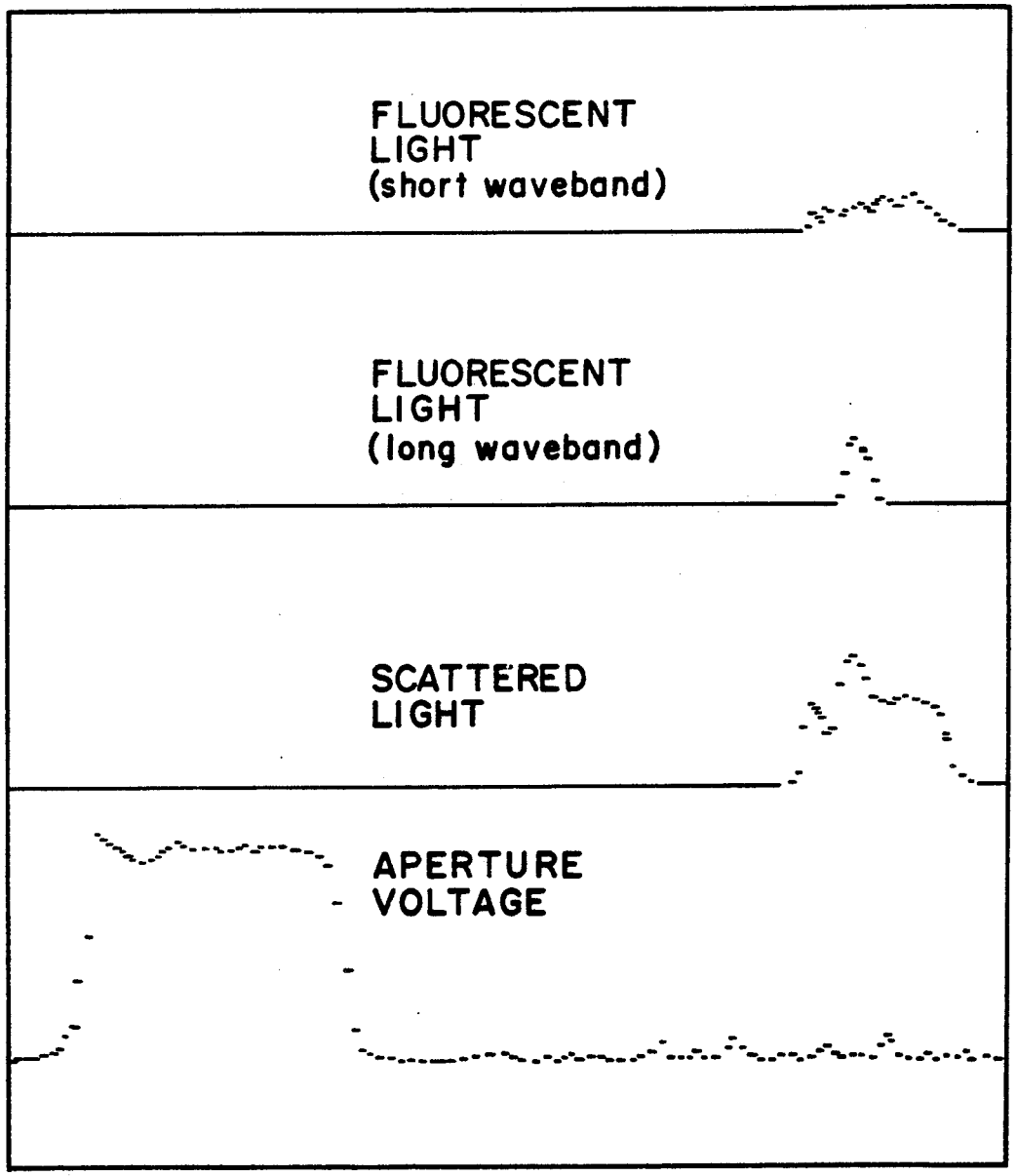
FIG. 4 shows typical waveforms resulting from particle detection.

In detail, the signals are amplified through a series of three amplifiers, providing four degrees of amplification which may be selected for optimum digitisation. After digitisation, signals are held in temporary memories 71 and 72 while other signals are being transferred by direct memory access to the main computer via bus 75. Waveforms having peak values within a preset range, or characteristics as described in the following paragraph, are stored until a certain number are counted and the volume pumped is noted. Then, gains are changed, more sample fluid pumped, and a different range of signal strengths recorded. This is continued until an entire over-range is handled. At a point within these ranges, flow shifts from a small sensor to a large one. Electrical volume, that is conductivity measurement, is usually the parameter which determines ranging, so that the system covers a complete spectrum of microscopic diameters, with a set number counted in each range. This provides particle information with the same statistical validity in each size range. Current particle counters typically generate counts of variable validity because of differences in the numbers counted in each range. In known apparatus, only the peak value of each signal is recorded, and the values are stored separately as counts in sets of channels ("channelysers"). In the system of this invention, four or more signals are digitized simultaneously at variable intervals (typically one microsecond) over the time the particle is in the sensing zone. This produces four or more stored waveforms, associated with each particle, which are retrieved and analysed later to identify the particle. The shapes of the waveforms and comparison between the signals for an individual particle are useful for making precise identification of types of particles. As an example of this, reference may be made to FIG. 4. The upper trace is from the green end of the fluorescent measurement spectrum and represents the entire particle. The next trace from the red end represents only a portion of the body which responds in this region of the spectrum. The scattered light trace shown next gives a measure of the surface characteristics of the body. The aperture voltage or volume measurement shown in the lower trace is typical of that for a smaller particle.

Peak detection is used for establishing signal ranges for digitisation. Peak values of signals are applied to threshold the gates whose output states are connected through programmable logic circuitry to panel display lights and alarm controls, and counting circuitry. In cases where particle identity can be determined by an algorithmic combination of the various peak values, this feature provides rapid indication of the presence of identified particles, without the need for waveform analysis. Algorithms are also be used in this way by the control logic board 77 to decide whether or not to store a given set of waveforms. In many cases, samples contain large numbers of particles which are of no interest. Rejection of their waveforms at this preliminary stage results in more efficient use of limited computer memory.

What is claimed is:

1. Apparatus for the detection and analysis of particles in a sample fluid, comprising: means defining a sample fluid flow path having a restriction immediately followed by a sensing zone downstream from and spaced from said restriction, wherein particles in the sample fluid traverse said restriction and said sensing zone one at a time; electrical sensing means measuring electrical conductivity variations in the flow path caused by the presence of a first particle in the restriction; means irradiating the sensing zone with a laser; first detector means responsive to light scattered by the same first particle when it reaches the sensing zone; second detector means responsive to fluorescence from the same first particle in the sensing zone; means digitizing and storing individually the signals from the electrical sensing means and from each of the detector means; and means displaying the stored signals as waveforms whereby the nature of the particle can be determined.

2. Apparatus as set out in claim 1, further including means comparing successive waveforms from each detector, whereby the presence of abnormal particles can be detected.

3. Apparatus as set out in claim 1, wherein said second detector means comprises a first detector responsive to shorter wavelengths and a second detector responsive to longer wavelengths in the fluorescence.

4. Apparatus as set out in claim 1 wherein the restriction in the flow path is provided by a flow cell having an aperture through which the sample fluid passes, the apparatus further including means providing a flow of a sheath fluid around the sample fluid.

5. Apparatus as set out in the claim 4 wherein the restriction in the flow path is provided by a selected one of first and second flow cells, the first flow cell having a smaller aperture then the second, the flow path including a screen through which the sample fluid flows before entering the first flow cell to remove particles larger than the aperture.

6. Apparatus as set out in claim 4, further including a collection tube downstream of the sensing zone to separate the sample fluid from the sheath fluid.

7. Apparatus as set out in claim 4 further including means for controlling back-pressure in the sensing zone to avoid bubble formation at the restriction and improve the sensitivity of the measurement of the electrical conductivity variations across the restriction.

8. Apparatus as set out in claim 2, wherein aid second detector means comprises a first detector responsive to shorter wavelength and a second detector responsive to longer wavelengths in the fluorescence.

9. Apparatus as set out in claim 5, further including a collection tube downstream of the sensing zone to separate the sample fluid from the sheath fluid.

10. A method for the detection and analysis of particles in a sample fluid comprising the steps of: defining a flow path for the fluid, the path including a restriction followed by a sensing zone immediately downstream from and spaced from the restriction, the restriction being traversed by the particles one at a time; measuring electrical conductivity variations in the flow path caused by the presence of a particle in the restriction; irradiating the sensing zone with a laser; detecting light scattered by said particle reaching the sensing zone to provide a scattered light output waveform; detecting fluorescence from said particle in the sensing zone to provide a fluorescence output waveform; digitizing and storing individually the output waveforms and the conductivity measurement; and displaying the stored waveforms and conductivity measurement whereby the nature of said particle can be determined.

11. A method as set out in claim 10 further including the step of measuring the peak value of the stored waveforms, comparing the peak value with a prescribed range and adjusting the flow rate of the sample fluid to cause the stored waveform to fit within the prescribed range.

12. A method as set out in claim 10 further including the steps of comparing successive waveforms from each detecting step whereby the presence of abnormal particles can be determined.

13. Apparatus for the detection and analysis of particles in a sample fluid, comprising: a flow cell having a restriction through which the sample fluid passes, and a sensing zone immediately downstream from and spaced from the restriction, said restriction and said sensing zone being traversed by the particles one at a time; means providing a flow of a sheath fluid around the sample fluid; electrode means causing a current to flow across the restriction; means sensing the resulting voltage across the restriction, to measure conductive variations in the fluid caused by the presence of a particle in the restriction; means irradiating the sensing zone with a laser; first detector means responsive to light scattered by the same particle in the sensing zone; second detector means responsive to fluorescence from the same particle in the sensing zone; and means digitizing and storing individual signals from the electrode means and each of the detector means, whereby the nature of the particle can be determined.

* * * * *